United States Patent
Thiel et al.

(10) Patent No.: US 12,351,563 B2
(45) Date of Patent: *Jul. 8, 2025

(54) REDUCTION OF THE ODOR OF MONOTHIOCARBONATE COMPOUNDS BY ADDITION OF OXIDANTS

(71) Applicant: BASF SE, Ludwigshafen am Rhein (DE)

(72) Inventors: Indre Thiel, Ludwigshafen am Rhein (DE); Thomas Maximilian Wurm, Ludwigshafen am Rhein (DE); Peter Rudolf, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 571 days.

This patent is subject to a terminal disclaimer.

(21) Appl. No.: 17/634,313

(22) PCT Filed: Aug. 13, 2020

(86) PCT No.: PCT/EP2020/072721
§ 371 (c)(1),
(2) Date: Feb. 10, 2022

(87) PCT Pub. No.: WO2021/028521
PCT Pub. Date: Feb. 18, 2021

(65) Prior Publication Data
US 2022/0289697 A1    Sep. 15, 2022

(30) Foreign Application Priority Data
Aug. 14, 2019 (EP) ..................... 19191796

(51) Int. Cl.
*C07D 277/14* (2006.01)
*C07D 327/04* (2006.01)

(52) U.S. Cl.
CPC ......... *C07D 277/14* (2013.01); *C07D 327/04* (2013.01)

(58) Field of Classification Search
CPC .................................................. C07D 327/04
See application file for complete search history.

(56) References Cited

U.S. PATENT DOCUMENTS 11,518,752 B2 * 12/2022 Thiel .................... C07D 327/04
2002/0082168 A1   6/2002 Graham et al.

FOREIGN PATENT DOCUMENTS

| CN | 107721973 A | 2/2018 |
| FR | 2893025 A1 | 5/2007 |
| JP | S53-105450 A | 9/1978 |
| WO | 2019/034468 A1 | 2/2019 |
| WO | 2019/034470 A1 | 2/2019 |
| WO | 2019/034473 A1 | 2/2019 |
| WO | WO-2019/034369 A1 | 2/2019 |
| WO | WO-2019/034469 A1 | 2/2019 |

OTHER PUBLICATIONS

International Search Report for PCT Patent Application No. PCT/EP2020/072721, Issued on Sep. 24, 2020, 3 pages.
Rao, et al., "Synthesis and Antispasmodic Activity of some New 6,8-Dibromo-2-[(alkyl/arylsulphono)methyl]-3-aryl-4 (3H)-Quinazolinones", Indian Journal of Pharmaceutical Sciences, vol. 48, Issue 1, May 17, 1985, pp. 13-15.
Written Opinion for PCT Patent Application No. PCT/EP2020/072721, Issued on Sep. 24, 2020, 5 pages.
International Preliminary Report on Patentability issued Feb. 8, 2022 in PCT/EP2020/072721, 7 pages.
Andy Wells, "Oxidation States of Alcohols and Related Functional Groups", Chapter 14.5, Chem 12A: Organic Chemistry, Chemistry LibreTexts, Jul. 2, 2011, 5 pages.
Jerry March, "Oxidations and Reductions", Chapter 19, Advanced Organic Chemistry: Reactions, Mechanisms, and Structure, Fourth Edition, 1929, pp. 1158-1159.
Office Action received for Japanese Application No. 2022-508782 mailed on Oct. 8, 2024, 8 pages with English translation.

* cited by examiner

*Primary Examiner* — Laura L Stockton
(74) *Attorney, Agent, or Firm* — Grüneberg and Myers PLLC

(57) ABSTRACT

A process reduces the odor of compounds with al least one five-membered cyclic monothiocarbonate group, referred to as monothiocarbonate compounds. The monothiocarbonate compounds are in are liquid phase and are brought into contact with an oxidant.

5 Claims, No Drawings

REDUCTION OF THE ODOR OF MONOTHIOCARBONATE COMPOUNDS BY ADDITION OF OXIDANTS

TITLE OF THE INVENTION

CROSS-REFERENCE TO RELATED APPLICATIONS

This application is the National Stage entry under § 371 of International Application No. PCT/EP2020/072721, filed on Aug. 13, 2020, and which claims the benefit of priority to European Application No. 19191796.2, filed on Aug. 14, 2019. The content of each of these applications is hereby incorporated by reference in its entirety.

BACKGROUND OF THE INVENTION

Field of the Invention

Object of the invention is a process to reduce the odor of compounds with at least one five-membered cyclic monothiocarbonate group wherein the organic sulfur compounds are in a liquid phase and are brought into contact with an oxidant.

Description of Related Art

Organic sulfur compounds are valuable compounds with various desired properties caused by the content of sulfur. They may be obtained by chemical reactions involving the use of mercaptanes, sulfur or sulfides as reactants.

However, the organic sulfur compounds obtained often have bad odor which is due to a content of undesired volatile by-products which probably comprise sulfur in form of mercapto groups or any unreacted starting materials with sulfur atoms.

An example of organic sulfur compounds are cyclic monothiocarbonates. A suitable synthesis for cyclic monothiocarbonates is described in WO 2019/034469 A1. However, the monothiocarbonates obtained have an unpleasant or nasty smell caused by sulfur comprising by-products.

The oxidation of sulfur compounds to the corresponding sulfoxide compounds with hydrogen peroxide is described by A. Devender Rao, C H. Ravishankar and V. Malla Reddy in Indian J. Pharm. Sci. 1986, 48 (1), pages 13 to 15. Table 1 on page 14 includes linear thiocarbonate compounds, see compounds II d and II j; these linear thiocarbonate compounds are easily oxidized.

It is an object of this invention to provide an easy and economic process to reduce the odor of organic sulfur compounds but maintain the sulfur compounds as such.

SUMMARY OF THE INVENTION

It has now been found that monothiocarbonate compounds having reduced odor may be obtained by a process using specific oxidants.

Accordingly, the invention relates to a process to reduce the odor of compounds with at least one five-membered cyclic monothiocarbonate group wherein the organic sulfur compounds are in a liquid phase and are brought into contact with an oxidant.

DETAILED DESCRIPTION OF THE INVENTION

To the monothiocarbonate compounds Compounds with at least one five-membered cyclic monothiocarbonate group are shortly referred to as "monothiocarbonate compounds".

Any reference to "monothiocarbonate compounds" shall include mixtures of different monothiocarbonate compounds, if not otherwise mentioned or obvious from the context.

The one five-membered cyclic monothiocarbonate group is preferably a ring system with 5 members, three of them are from the monothiocarbonate —O—C(=O)—S— and the further two members are carbon atoms closing the five-membered cycle.

The monothiocarbonate compounds may comprise, for example, up to 1000, in particular up to 500, preferably up to 100 five-membered cyclic monothiocarbonate groups.

In a preferred embodiment the monothiocarbonate compounds comprise 1 to 10, notably 1 to 5 five-membered cyclic monothiocarbonate groups. In a most preferred embodiment the monothiocarbonate compounds comprise 1 to 3, particularly 1 or 2 five-membered cyclic monothiocarbonate groups.

The monothiocarbonate compounds may have, for example, a molecular weight of up to 500.000 g/mol. Preferred monothiocarbonate compounds have a molecular weight of up to 1000 g/mol. Most preferred are compounds having a molecular weight of up to 500 g/mol.

In a preferred embodiment the monothiocarbonate compounds do not comprise any primary or secondary amino groups.

In a particularly preferred embodiment, the monothiocarbonate compounds do not comprise other functional groups than monothiocarbonate groups, carboxylic ester groups or ether groups or chloride.

The term "chloride", as used herein, is the trivial name of a covalently bonded Cl atom.

Suitable monothiocarbonate compounds with one five-membered cyclic monothiocarbonate group are disclosed in WO 2019/034470. Preferred monothiocarbonate compounds with one five-membered cyclic monothiocarbonate group are compounds of formula (I)

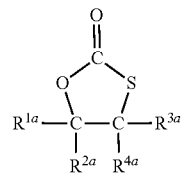

with $R^{1a}$ to $R^{4a}$ independently from each other representing hydrogen or an organic group with up to 50 carbon atoms, whereby, alternatively, $R^{2a}$, $R^{4a}$ and the two carbon atoms of the monothiocarbonate group may also together form a five to ten membered carbon ring.

Suitable monothiocarbonate compounds with more than one five-membered cyclic monothiocarbonate group are, for example, disclosed in WO 2019/034473 A1. Preferred monothiocarbonate compounds with more than one five-membered cyclic monothiocarbonate group are compounds of formula (II)

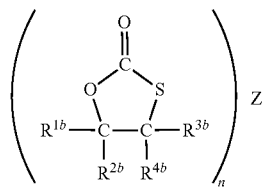

with $R^{1b}$ to $R^{4b}$ independently from each other representing hydrogen or an organic group with up to 50 carbon atoms, whereby, alternatively, $R^{2b}$, $R^{4b}$ and the two carbon atoms of the monothiocarbonate group may also together form a five to ten membered carbon ring and one of the groups $R^{1b}$ to $R^{4b}$ is a linking group to Z, n representing an integral number of at least 2, and Z representing a n-valent organic group.

Various processes are known for the preparation of monothiocarbonate compounds.

According to U.S. Pat. Nos. 3,072,676 and 3,201,416 ethylene monothiocarbonates may be prepared by a two-step-process. In a first step mercaptoethanol and chlorocarboxylates are reacted to give hydroxyethylthiocarbonate, which is heated in the second step in the presence of a metal salt catalyst to the ethylene monothiocarbonate.

According U.S. Pat. No. 3,517,029 alkylene monothiocarbonates are obtained by reacting mercaptoethanol and a carbonate diester in the presence of a catalytically active salt of thorium.

According to the process disclosed in U.S. Pat. No. 3,349,100 alkylene monothiocarbonates are obtained by reacting an epoxide with carbonyl sulfide.

A synthesis using phosgene as starting material is known from U.S. Pat. No. 2,828,318. Phosgene is reacted with hydroxymercaptanes.

Preferably, the monothiocarbonate compounds used in the process for the purification as defined above are compounds that are obtained as product from a process comprising
  reacting a compound with at least one epoxy group or at least one halohydrin group with phosgene or an alkylformate to give an adduct, and
  then reacting the adduct with a compound comprising anionic sulfur,
  optionally followed by a further work-up of the obtained crude product by extraction or distillation The above process is disclosed in WO 2019/034469 A1 (first step reaction with epoxy compound) and in PCT patent application with application no. PCT/EP2020/051110 (first step reaction with halohydrin).

The monothiocarbonate compounds obtained usually comprise by-products with a content of sulfur. Such by-products cause a very nasty smell. Often such by-products cannot be totally removed by a standard work-up involving process steps such as distillation or one or more extractions, which are notably extractions with a base such as, for example, aqueous $NaHCO_3$. The odor of the monothiocarbonate compounds is usually still bad after such standard work-up.

The monothiocarbonate compounds used for the process are in a liquid phase.

The monothiocarbonate compounds obtained from the preparation process may be liquid or solid at 21° C., 1 bar.

Monothiocarbonate compounds, that are liquid at 21° C., 1 bar may be used as such, without solvent.

Monothiocarbonate compounds, that are solid at 21° C., 1 bar are preferably used in form of a solution.

Suitable solvents for solid monothiocarbonate compounds are protic solvents or notably aprotic solvents.

The aprotic solvents may be hydrophobic, such as, for example, hydrocarbons, including aromatic hydrocarbons and chlorinated hydrocarbons, for example, toluene, chlorobenzene or dichloro-benzene, chloroform, or hydrophilic such as, for example, acetonitrile or dimethyl sulfoxide or esters or ethers like tetrahydrofuran, dioxane, polyether or glymes.

To the process

The monothiocarbonate compounds are brought into contact with an oxidant.

The term "oxidant" shall include a single oxidant or a mixture of different oxidants.

Suitable oxidants are notably oxygen, ozone, hydrogen peroxide and any other inorganic compounds with a high content of oxygen such as, for example, nitrogen compounds comprising oxygen such as nitrogen dioxide, nitric acid or any salts thereof or notably inorganic peroxides.

Such inorganic peroxides may be acids or salts, notably metal salts with an anion selected from perchlorate, permanganate, perchromate, hypochlorite or perborate, preferably perchlorate, permanganate or perborate.

Particularly preferred oxidants are hydrogen peroxide and nitric acid ($HNO_3$).

Most preferred is hydrogen peroxide.

The oxidant is preferably used in form of a solution, particularly in form of an aqueous solution. The concentration of the oxidant in the aqueous solution is preferably less than 50%, more preferably less than 40% by weight. Preferably, the concentration of the oxidant in the aqueous solution is at least 5, more preferably at least 10% by weight.

The oxidant is preferably used in an amount of at least 5 mol, notably at least 10 mol per 100 mol of organic sulfur compounds.

The oxidant is preferably used in an amount of at maximum 40 mol, notably of at maximum 30 mol, more preferably of at maximum 20 mol per 100 mol of organic sulfur compounds, i.e., monothiocarbonate compounds.

The oxidant may be brought into contact with the organic sulfur compounds, i.e., monothiocarbonate compounds, in any suitable manner.

In a preferred embodiment of the process, the oxidant is added to the organic sulfur compounds, i.e., monothiocarbonate compounds, which are in a liquid state.

The contact of the oxidant and the organic sulfur compounds, i.e., monothiocarbonate compounds, is preferably at a temperature of at least 20° C., notably of at least 30° C., more preferably of at least 40° C. and most preferably of at least 50° C., in particular of at least 55° C. Preferably, the temperature is at maximum 150° C., notably at maximum 100° C.

The contact period is preferably from 5 minutes to 10 hours, more preferably from 10 minutes to 6 hours, more preferably from 20 minutes to 3 hours and most preferably from 30 minutes to 2 hours.

Any solvents used in combination with the organic sulfur compounds, i.e., monothiocarbonate compounds may be removed, for example, by distillation.

The process of this invention may be a batch process, a semi-continuous process or a continuous process. In a continuous process all starting materials are fed continuously to the reactor and all products are removed continuously, whereby the oxidant may be separated from the product streams by usual means, such as distillation, filtration or precipitation or by a decomposition reaction, as the case may be.

The process of this invention may be used in combination with other processes for purification and reduction of odor, such as an extraction process, for example, extraction with a base, such as aqueous $NaHCO_3$, an adsorption process, for example, with metal oxides as adsorbents or a process in which by-products are removed or turned into unproblematic compounds by chemical reactions.

The monothiocarbonate compounds, obtained from the process have a significantly reduced odor. The oxidation process has obviously no significant impact on the monothiocarbonates themselves, no oxidation of the monothiocarbonate compounds themselves was observed. The oxidation process seems to have a major impact on undesired, possibly volatile by-products which result from the synthesis process, only. An oxidation of the organic sulfur compounds themselves is not or hardly observed. Usually, less than 10 mol %, notably less than 5 mol % most preferably less than 2, respectively less than 1 mol % of the monothiocarbonate compounds, react themselves with the oxidant and are transferred into oxidation products.

EXAMPLES

Synthesis of 5-[4-[(2-oxo-1,3-oxathiolan-5-yl)methoxyl]butoxymethyl]-1,3-oxathiolan-2-One of Formula

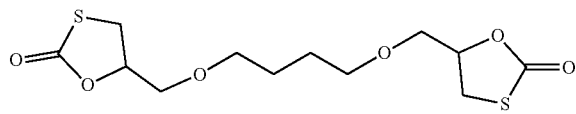 [SMILES: O=C1OC(COCCCCOCC2CSC(=O)O2)CS1]

which is shortly referred to as butanediol-dithiocarbonate or BDO-TC

The synthesis was made according to the process disclosed in WO 2019/034469 A1.

In the first step of the synthesis, the epoxide 1,4-butanediol-diglycidylether was reacted with phosgene as described in WO 2019/034469 A1.

In the second step, the obtained ρ-chloroalkyl chloroformiate ([2-chloro-1-[4-(3-chloro-2-chlorocarbonyloxy-propoxy)butoxymethyl]ethyl] carbonochloridate) (845 g, 2.1 mol) and dichloromethane (2.5 L) were placed in a 8 liter reactor. The solution was cooled down to 0° C. before Na$_2$S (2.2 eq., 15 wt % aqueous solution) was slowly added, maintaining the temperature at 5° C. After the complete addition the reaction mixture was allowed to warm to room temperature and stirred for 1 hour. The phases were separated, and the aqueous phase was extracted with dichloromethane (1×0.5 L). The combined organic phase was extracted with water (3×0.5 L), dried over Na$_2$SO$_4$ and filtered over Celite 545 (300 g per kg initial chloroformiate). The solvent was removed from the organic phase under reduced pressure and the desired product was obtained as a clear viscous liquid (656 g, 96%).

The above synthesis was made for two different grades of 1,4-butanediol-diglycidylether.

One grade is a relatively pure grade with a minor content of other epoxides, notably epoxides of higher molecular weight.

The other grade was a technical grade comprising a significant content of other epoxides.

Accordingly, two different products were obtained from the synthesis.

One product, referred to as "pure BDO-TC", having a content of BDO-TC of 84.2 area %, measured by gas chromatography.

A second product, referred to as "technical BDO-TC", having a content of BDO-TC of 61.3 area %, measured by gas chromatography.

Examples 1 to 8: Oxidation

The respective BDO-TC (5 g) was dissolved in toluene (10 g) and an aqueous solution of the oxidant (30% by weight H$_2$O$_2$ in water; 0.1 molar aqueous solution of KMnO$_4$) was added. The mixture was stirred for 30 min at the respective temperature. After phase separation the organic phase was washed twice with water (v/v 1:1) at the same temperature. After the last phase separation toluene was removed from the organic phase under reduced pressure, yielding the BDO-TC as a viscous liquid.

The solution of KMnO$_4$ was used in an amount of 1 volume per volume of the BDO-TC. The solution of H$_2$O$_2$ was used in an amount of 10 mol H$_2$O$_2$ per 100 mol of BDO-TC.

The gas chromatograms of the BDO-TC obtained after oxidation showed no additional peaks that relate to oxidation products of the BDO-TC itself.

Testing

The odor of the BDO-TC obtained was tested immediately thereafter. The samples were tested at room temperature by 3 different people. The participants reported their olfactoral assessment according to the following classification scheme:
 1: odorless
 2: slight stale odor
 3: slight "mercaptan odor"
 4: "mercaptan odor"
 5: distinct "mercaptan odor"

Before the treatment with the oxidant, the pure BDO-TC had an odor of classification 4. Before the treatment with the oxidant, the technical BDO-TC had an odor of classification 5.

TABLE 1 purification by oxidation

| Example | BDO-TC | Conditions | Color after oxidation | Odor after oxidation |
|---|---|---|---|---|
| 1 | "pure" | H$_2$O$_2$ 25° C. | clear liquid | 2 |
| 2 | technical | H$_2$O$_2$ 25° C. | clear liquid | 2 |
| 3 | "pure" | H$_2$O$_2$ 40° C. | clear liquid | 2 |
| 4 | technical | H$_2$O$_2$ 40° C. | clear liquid | 3 |
| 5 | "pure" | H$_2$O$_2$ 60° C. | clear liquid | 2 |
| 6 | technical | H$_2$O$_2$ 60° C. | turbid liquid | 2 |
| 7 | "pure" | KMnO$_4$ 25° C. | clear liquid | 2-3 |
| 8 | technical | KMnO$_4$ 25° C. | turbid liquid | 2-3 |

Examples 9 to 12: Combinations of Oxidation with Other Treatments a) Combination of oxidation with removal of impurities by chemical reaction (Michael addition to double bond)

The respective BDO-TC (5 g) was dissolved in toluene (10 g) and methylmethacrylate (MMA) was added. The mixture was stirred for 30 min at 25° C. Then H$_2$O$_2$ (30% aqueous solution) was added at 25° C. and the mixture was stirred for further 30 min. After phase separation the organic phase was extracted with water (v/v 1:1). All volatiles and toluene were removed from the organic phase under reduced pressure, yielding the BDO-TC as a viscous liquid.

b) Combination of oxidation with extraction

The respective BDO-TC (5 g) was dissolved in toluene (10 g) and extracted twice with an aqueous NaHCO$_3$ solution at 25° C. (v/v 1:1) followed by the extraction with water (v/v 1:1). Then $H_2O_2$ (30% aqueous solution) was added at 25° C. and the mixture was stirred for further 30 min. After phase separation the organic phase was extracted with water (v/v 1:1). All volatiles and toluene were removed from the organic phase under reduced pressure, yielding the BDO-TC as a viscous liquid.

TABLE 2

Purification by oxidation in combination with chemical reaction or extraction

| Example | BDO-TC | conditions | Color after oxidation | Odor after oxidation |
|---|---|---|---|---|
| 1 | pure | 10 mol % MMA + 10 mol % $H_2O_2$ | clear liquid | 1 |
| 2 | technical | 10 mol % MMA + 10 mol % $H_2O_2$ | clear liquid | 2 |
| 3 | pure | $NaHCO_3$ (0.5M) + 10 mol % $H_2O_2$ | clear liquid | 2 |
| 4 | technical | $NaHCO_3$ (0.5M) + 10 mol % $H_2O_2$ | clear liquid | 3 |

The inventio claimed is:

1. A process to reduce the odor of compounds with at least one five-membered cyclic monothiocarbonate group, the process comprising:
   contacting a compound with at least one five-membered cyclic monothiocarbonate group, in a liquid phase, with an oxidant;
   wherein the compound with at least one five-membered cyclic monothiocarbonate group is a compound of formula (I)

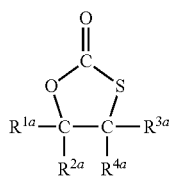

with $R^{1a}$ to $R^{4a}$ independently from each other representing hydrogen or an organic group with up to 50 carbon atoms, whereby, alternatively, $R^{2a}$, $R^{4a}$ and the two carbon atoms of the monothiocarbonate group together form a five to ten membered carbon ring; or
   a compound of formula (II)

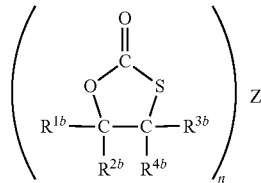

with $R^{1b}$ to $R^{4b}$ independently from each other representing hydrogen or an organic group with up to 50 carbon atoms, whereby, alternatively, $R^{2b}$, $R^{4b}$ and the two carbon atoms of the monothiocarbonate group together form a five to ten membered carbon ring, and one of $R^{1b}$ to $R^{4b}$ is a linking group to Z, n represents an integral number of at least 2, and Z represents a n-valent organic group; or
   a mixture of compounds of formulae (I) and (II).

2. The process according to claim 1, wherein the compound with at least one five-membered cyclic monothiocarbonate group is obtained as a product from a process comprising:
   reacting a compound with at least one epoxy group or at least one halohydrin group with phosgene or an alkylformate, to give an adduct,
   reacting the adduct with a compound comprising anionic sulfur, to obtain a crude product, and
   optionally, further working-up the obtained crude product by extraction or distillation.

3. The process according to claim 1, wherein the oxidant is hydrogen peroxide.

4. The process according to claim 1, wherein the oxidant and the compound with at least one five-membered cyclic monothiocarbonate group are brought into contact at 10 to 100° C.

5. The process according to claim 4, wherein a contact period is from 5 minutes to 10 hours.

* * * * *